(12) United States Patent
Didsbury et al.

(10) Patent No.: US 9,248,098 B2
(45) Date of Patent: Feb. 2, 2016

(54) TREATING OR PREVENTING PAIN USING SPICAMYCIN DERIVATIVES

(75) Inventors: John R. Didsbury, Raleigh, NC (US); Kenneth J. Ingold, Durham, NC (US); Linda Goff Jet, Hillsborough, NC (US); Andrew Xian Chen, San Diego, CA (US); Hailiang Chen, San Diego, CA (US)

(73) Assignee: DARA BIOSCIENCES, INC., Raleigh, NC (US)

( * ) Notice: Subject to any disclaimer, the term of this patent is extended or adjusted under 35 U.S.C. 154(b) by 793 days.

(21) Appl. No.: 13/122,771

(22) PCT Filed: Oct. 9, 2009

(86) PCT No.: PCT/US2009/005550
§ 371 (c)(1),
(2), (4) Date: Jun. 9, 2011

(87) PCT Pub. No.: WO2010/042212
PCT Pub. Date: Apr. 15, 2010

(65) Prior Publication Data
US 2011/0237536 A1  Sep. 29, 2011

Related U.S. Application Data

(60) Provisional application No. 61/104,359, filed on Oct. 10, 2008, provisional application No. 61/182,138, filed on May 29, 2009.

(51) Int. Cl.
| | |
|---|---|
| *A01N 43/04* | (2006.01) |
| *A61K 31/70* | (2006.01) |
| *C07H 19/04* | (2006.01) |
| *C07H 19/20* | (2006.01) |
| *A61K 9/107* | (2006.01) |
| *A61K 31/7076* | (2006.01) |

(52) U.S. Cl.
CPC ........... *A61K 9/1075* (2013.01); *A61K 31/7076* (2013.01)

(58) Field of Classification Search
CPC ......................... A61K 31/7076; A61K 9/1075
See application file for complete search history.

(56) References Cited

U.S. PATENT DOCUMENTS

| 5,461,036 A | 10/1995 | Otake et al. |
| 5,631,238 A | 5/1997 | Otake et al. |
| 5,905,069 A | 5/1999 | Borsook et al. |
| 6,239,102 B1 | 5/2001 | Tiemessen et al. |
| 7,196,071 B2 | 3/2007 | Borsook |
| 7,375,094 B2 | 5/2008 | Borsook |
| 7,632,825 B2 | 12/2009 | Borsook |
| 2004/0038927 A1 | 2/2004 | Borsook |
| 2006/0257434 A1 | 11/2006 | Mugerditchian et al. |
| 2007/0071777 A1 | 3/2007 | Bromer et al. |
| 2008/0207557 A1 | 8/2008 | Borsook |

FOREIGN PATENT DOCUMENTS

| EP | 0525479 A1 | 2/1993 |
| JP | 2006-527736 A | 12/2006 |
| JP | 2007-246543 A | 9/2007 |
| JP | 2008-536919 A | 9/2008 |
| WO | WO 2007/064926 A2 | 6/2007 |
| WO | WO 2008/070538 A2 | 6/2008 |
| WO | WO 2009/012303 A2 | 1/2009 |

OTHER PUBLICATIONS (R) M. A. Longer, "Sustained-Release Drug Delivery Systems," Chapter 91 in Remington's Pharmaceutical Sciences, 18th Edition, Gennaro et al (eds.), Mack Publishing Co., Easton, PA, 1990, only pp. 1676-1693 supplied. See pp. 1688 and pp. 1691-1692 for discussions of "Emulsions," "Nanoparticles" and "Liposomes."*
Abdi S. et al., "The Effects of KRN5500, a Spicamycin Derivative, on Neuropathic and Nociceptive Pain Models in Rats" *Anesthesia & Analgesia*, 2000;91:955-959.
Borsook, D. et al., "Antineuropathic Effects of the Antibiotic Derivative Spicamycin KRN5500", *Pain Medicine*, vol. 5, No. 1, 2004, pp. 104-108.
Igarashi E., "Factors Affecting Toxicity and Efficacy of Polymeric Nanomedicines", *Toxicology and Applied Pharmacology*, vol. 229, Issue 1, pp. 121-134, May 15, 2008.
International Preliminary Report on Patentability Corresponding to International Application No. PCT/US2009/005550; Date of Mailing: Apr. 21, 2011; 7 pages.
International Search Report Corresponding to International Application No. PCT/US2009/005550; Date of Mailing: Jun. 23, 2010; 13 pages.
Kobierski L.A. et al., "A Single Intravenous Injection of KRN5500 (Antibiotic Spicamycin) Produces Long-Term Decreases in Multiple Sensory Hypersensitivities in Neuropathic Pain", *Anesthesia & Analgesia*, 2003;97:174-182.
Matsumura, Y. et al., "Reduction of the Side Effects of an Antitumor Agent, KRN5500, by Incorporation of the Drug into Polymeric Micelles", *Japanese Journal of Cancer Research*, vol. 90, No. 1., Jan. 1999, pp. 122-128.
DiLorenzo L et al: "A Water-Soluble Synthetic Spicamycin Derivative (San-Gly) Decreases Mechanical Allodynia in a Rodent Model of Neuropathic Pain", Neuroscience Letters, Sep. 13, 2002, pp. 37-40, vol. 330, No. 1, Limerick, IE.
Mizumura, Y., et al., "Incorporation of the Anticancer Agent KRN5500 into Polymeric Micelles Diminishes the Pulmonary Toxicity," *Japanese Journal of Cancer Research*, Nov. 2002, pp. 1237-1243, vol. 93.
Mizumura, Y., "Spicamycin Derivative," *Nippon Rinsho*, Feb. 2006, pp. 322-328, vol. 64(2). [Abstract, Tables, Figures and References in English].

* cited by examiner

*Primary Examiner* — Lawrence E Crane
(74) *Attorney, Agent, or Firm* — Alston & Bird LLP

(57) ABSTRACT

The present invention relates to a pharmaceutical composition comprising spicamycin derivatives that vary in their fatty acid side chain moieties and are useful in the treatment of pain. The invention further provides a method of using the pharmaceutical composition to treat pain, including neuropathic pain.

11 Claims, No Drawings

TREATING OR PREVENTING PAIN USING SPICAMYCIN DERIVATIVES

RELATED APPLICATIONS

This application is a 35 U.S.C. §371 national phase application of PCT Application PCT/US2009/005550, filed Oct. 9, 2009, which claims the benefit under 35 U.S.C. §119(e) of U.S. Provisional Application Ser. No. 61/104,359, filed Oct. 10, 2008 and U.S. Provisional Patent Application Ser. No. 61/182,138, filed May 29, 2009. The entire contents of each of these applications is incorporated herein by reference.

FIELD OF THE INVENTION

The present invention relates to the use of spicamycin derivatives for treatment and/or prevention of pain, including neuropathic pain. The invention further relates to pharmaceutical compositions of spicamycin derivatives suitable for treatment or prevention of pain.

BACKGROUND OF THE INVENTION

Neuropathic pain is a chronic pain that results from nerve damage, is characterized by an abnormal hypersensitivity to innocuous as well as noxious stimuli, and often persists after the tissue damage and inflammation that initially caused the pain have healed. Eleven million patients worldwide are afflicted by neuropathic pain (Olsen, *WWMR, Inc. Consulting and Marketing Report* (2002)). Clinically, neuropathic pain is difficult to manage, fails to respond to standard analgesic treatments, and often worsens over time (Amer et al., *Acta Anaesthesiol. Scand.* 29:32 (1985); Cherny et al., *Neurology* 44:857 (1994)).

Spicamycin is an anti-tumor antibiotic produced by the bacterium *Streptomyces alansinicus* 879-MT$_3$ (Hayakawa et al. *Agric. Biol. Chem.* 49:2685 (1985)). The naturally occurring compound has the following general structure of Formula I, varying solely in the fatty acid moiety.

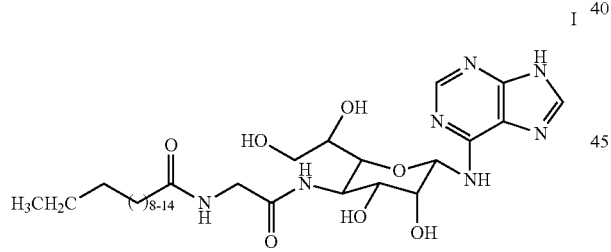

Synthetic spicamycin derivatives and their use as anti-tumor agents are described in U.S. Pat. Nos. 5,461,036 and 5,631,238 to Otake et al. The use of spicamycin or derivatives thereof, including KRN5500, to reduce and/or prevent pain is described in U.S. Pat. Nos. 5,905,069, 7,196,071, and 7,375,094 to Borsook et al. KRN5500 has been demonstrated to be effective in rat models of neuropathic pain (Abdi et al., *Anesth. Analg.* 91:955 (2000); Kobierski et al., *Anesth. Analg.* 97:174 2003).

The present invention provides improved compositions and methods for treating or preventing pain, e.g., neuropathic pain using spicamycin derivatives.

SUMMARY OF THE INVENTION

The present invention provides methods of treating and preventing pain, e.g., neuropathic pain, in a subject, comprising administering to a subject in need thereof certain derivatives of spicamycin. Also provided are pharmaceutical compositions comprising one or more compounds that are spicamycin derivatives.

Accordingly, as one aspect, the invention provides methods for treating or preventing pain, e.g., neuropathic pain, in a subject, comprising administering to a subject in need thereof, a treatment or prevention effective amount of a compound of Formula II:

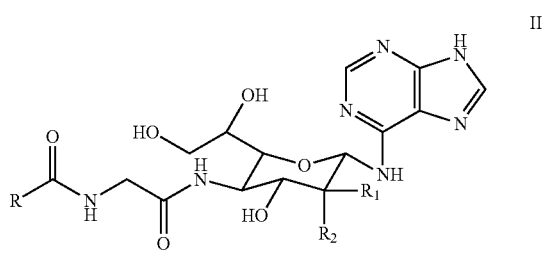

wherein $R_1$ and $R_2$ are different from each other and represent H or OH, and R represents a substituted or unsubstituted alkyl, alkenyl, alkynyl, or cycloalkyl;

or a pharmaceutically acceptable salt, prodrug, or optical isomer thereof.

The invention also provides methods for treating or preventing pain, e.g., neuropathic pain, in a subject, comprising administering to a subject in need thereof, a treatment or prevention effective amount of a compound of Formula II:

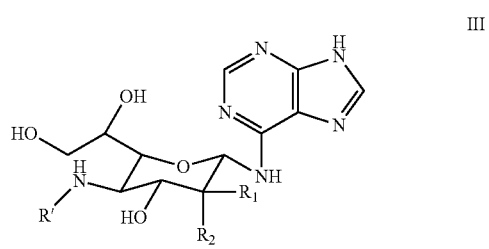

wherein $R_1$ and $R_2$ are different from each other and represent H or OH, and R' represents (I) a substituted or unsubstituted alkyl or alkenyl having one or two carbon atoms, or (2) H; or a pharmaceutically acceptable salt, prodrug, or optical isomer thereof.

As yet a further aspect, the invention provides methods for treating or preventing pain, e.g., neuropathic pain, in a subject, comprising administering to a subject in need thereof, a treatment or prevention effective amount of a compound of Formula IV:

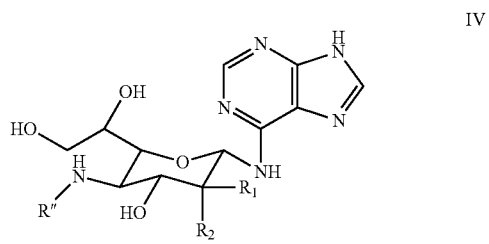

wherein $R_1$ and $R_2$ are different from each other and represent H or OH, each R" group can independently be an H or alkyl, alkenyl, alkynyl, or cycloalkyl group having 1 to 5 carbon atoms substituted with 1 to 3 independent $R^3$ or $R^4$;

each $R^3$ is independently heterocyclyl or heteroaryl, either optionally substituted with 1-3 independent $R^5$;

each $R^4$ is independently halogen, oxygen, sulfur, $CF_3$, $SR^6$, $OR^6$, $OC(O)R^6$, $NR^6R^6$, $NR^6R^7$, $COOR^6$, $C(O)R^6$, or $C(O)NR^6R^6$;

each $R^5$ is independently $C_1$-$C_{10}$ alkyl; halo; haloalkyl; $SR^6$; $OR^6$; $NR^6R^6$; $COOR^6$; $NO_2$; $CN$; $C(O)R^6$; $C(O)NR^6R^6$; $OC(O)R^6$; $S(O)_2R^6$; $S(O)_2NR^6R^6$; $NR^6C(O)NR^6R^6$; $NR^6C(O)R^6$; $NR^6(COOR^6)$; $NR^6C(O)R^8$; $NR^6S(O)_2NR^6R^6$; $NR^6S(O)_2R^6$; $NR^6S(O)_2R^8$; or $C_1$-$C_{10}$ alkyl substituted with $R^4$ or $R^8$;

each $R^6$ is independently H, $C_1$-$C_{10}$ alkyl; $C_2$-$C_{10}$ alkenyl; $C_2$-$C_{10}$ alkynyl; $C_3$-$C_{10}$ cycloalkyl; $R^8$; or $C_1$-$C_{10}$ alkyl substituted with $R^8$;

each $R^7$ is independently $COOR^9$, $C(O)NR^9R^9$, $S(O)_2R^9$; or $S(O)_2NR^9R^9$;

each $R^8$ is independently aryl, heteroaryl, or heterocyclyl; and each $R^9$ is independently H, $C_1$-$C_{10}$ alkyl, aryl, heteroaryl, or heterocyclyl;

or a pharmaceutically acceptable salt, prodrug, or optical isomer thereof.

In one embodiment of the invention, the neuropathy is selected from the group consisting of chemotherapy-induced neuropathy, cancer-related neuropathy, HIV-related peripheral neuropathy, post-herpetic neuralgia, diabetic neuropathy, sciatica, fibromyalgia, chronic fatigue syndrome pain, multiple sclerosis pain, complex regional pain syndrome type I, complex regional pain syndrome type II, central pain syndrome, painful traumatic mononeuropathy, post surgical pain syndrome, post mastectomy syndrome, post thoracotomy syndrome, phantom pain, nerve root avulsion, post radiation neuropathy, repetitive movement nerve injury, repetitive stress injury, and post injury neuropathy.

In another aspect of the invention, the compound of Formula II, III, or IV is administered concurrently with a further agent, e.g., an analgesic, anti-inflammatory, chemotherapeutic, anti-emetic, or peroxisome proliferator-activated receptor (PPAR) agonist compounds.

As still another aspect, the invention provides a pharmaceutical composition comprising a compound of Formula II, III, or IV or a pharmaceutically acceptable salt or prodrug thereof or an optical isomer thereof in a pharmaceutically acceptable carrier, e.g., in the form of a nanoemulsion or other nanoparticle.

In a further aspect, the invention provides a pharmaceutical composition comprising a compound of Formula II, III, or IV or a pharmaceutically acceptable salt or prodrug thereof or an optical isomer thereof in a formulation comprising a nanoemulsion formulation containing about 10 to about 15 weight % oil phase, about 5 to about 10 weight % surfactant, and about 50 to about 70 weight % aqueous phase, e.g., about 13 to about 15 weight % oil phase, about 6 to about 8 weight % surfactant, and about 55 to about 65 weight % aqueous phase. In one embodiment, the nanoemulsion contains about 7 weight % soybean oil, about 7 weight % MIGLYOL 812, about 7 weight % soy lecithin, about 0.3 weight % sodium oleate, and about 62 weight % water. In another embodiment, the nanoemulsion contains about 7 weight % soybean oil, about 7 weight % MIGLYOL 812, about 7 weight % soy lecithin, about 0.3 weight % sodium oleate, about 0.006 weight % EDTA, about 17 weight % sucrose, and about 62 weight % water.

The present invention is explained in greater detail in the drawings herein and the specification set forth below.

DETAILED DESCRIPTION OF THE INVENTION

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

DEFINITIONS

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

The term "treatment effective amount" or "effective amount," as used herein, refers to that amount of a composition of this invention that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, a therapeutically effective amount or effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, etc., as would be well known in the art.

"Prevent" or "preventing" or "prevention" refer to prevention or delay of the onset of the disorder and/or a decrease in the level of pain in a subject relative to the level of pain that would develop in the absence of the methods of the invention. The prevention can be complete, e.g., the total absence of pain in a subject. The prevention can also be partial, such that the occurrence of pain in a subject is less than that which would have occurred without the present invention.

Methods of assessing pain or pain relief are known in the art (e.g., subjective evaluation of pain by a patient), and standard animal models of pain are available such as the Randall Selitto or Bennet Xie rat models for pain; experimentally produced segmental spinal nerve injury or chronic constriction nerve injury (see, e.g., Kim et al., *Pain* 50:355 (1992); Bennett et al., *Pain* 33:87 (1988) and U.S. Patent Publication 2004/0038927); see also, Abdi et al., *Anesth. Analg.* 91:955 (2000). Models of neuropathic pain are also described in Zeltser et al., *Pain* 89:19 (2000); Seltzer et al., *Pain* 43:205 (1990); and Decosterd et al., *Pain* 87:149 (2000).

The term "neuropathic pain" is understood in the art and encompasses pain arising from injury to or pathological changes in the central nervous system and/or peripheral nervous system (reviewed in Woolf, *Acta Neurochir* 58:125 (1993)). Patients with neuropathic pain typically present with a characteristic set of sensory disorders independent of the cause, including a constant scalding or burning pain, a partial loss of sensitivity, tactile or cold allodynia and/or hyperpathia to repeated stimulation. Neuropathic pain arises from a number of diverse conditions, the most common of which are trigeminal neuralgia, postherpetic neuralgia, painful diabetic neuropathy, and the reflex sympathetic dystrophies including causalgia, mononeuropathies, and peripheral nerve injury. In general, neuropathic pain tends to be resistant to opioids and non-steroidal anti-inflammatories (NSAIDS), whereas nociceptive pain usually responds well to both of these treatment modalities. Few non-surgical alternatives exist for a patient with a disabling pain resistant to opioid drugs.

"Pharmaceutically acceptable," as used herein, means a material that is not biologically or otherwise undesirable, i.e., the material can be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science;* 20 ed. 2005). Exemplary pharmaceutically acceptable carriers for the compositions of this invention include, but are not limited to, sterile pyrogen-free water and sterile pyrogen-free physiological saline solution.

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

The term "alkyl" denotes a straight or branched hydrocarbon chain containing 1-24 carbon atoms, e.g., 1-12 carbon atoms. Examples of alkyl group include methyl, ethyl, propyl, isopropyl, butyl, isobutyl, tert-butyl, and the like.

The term "alkenyl" denotes a straight or branched hydrocarbon chain containing 1-24 carbon atoms, e.g., 1-12 carbon atoms, and containing one or more double bonds, e.g., 1, 2, 3, or 4 double bonds.

The term "alkynyl" denotes a straight or branched hydrocarbon chain containing 1-24 carbon atoms, e.g., 1-12 carbon atoms, and containing one or more triple bonds, e.g., 1, 2, 3, or 4 triple bonds.

The term cycloalkyl refers to non-aromatic cyclic hydrocarbon moieties containing 3-24 carbon atoms, e.g., 3-12 carbon atoms. The cycloalkyl group can contain one or more double bonds. Examples include cyclopropyl, cyclobutyl, cyclopentyl, and cyclohexyl.

By "substituted alkyl" is meant an alkyl in which an atom of the alkyl is substituted with, for example, a carbon, nitrogen, sulfur, oxygen, silicon, or halogen atom, or alternatively a nitrogen, sulfur, oxygen, or halogen atom. The term encompasses substituents on alkyl, alkenyl, alkynyl, and cycloalkyl groups.

Examples of substituents that can be attached to any atom of the alkyl group in a "substituted alkyl" include cyclyl groups, heterocyclyl groups; aryl groups, heteroaryl groups, amino groups, amido groups, nitro groups, cyano groups, azide groups, hydroxy groups, alkoxy groups, acyloxy groups, thioalkoxy groups, acyl thioalkoxy groups, halogen groups, sulfonate groups, sulfonamide groups, ester groups, carboxylic acids, oxygen (e.g., a carbonyl group), and sulfur (e.g., a thiocarbonyl group). Substituents also include any chemical functional group that imparts improved water-solubility to the molecule (e.g., carboxylic acid, carboxylic ester, carboxamido, morpholino, piperazinyl, imidazolyl, thiomorpholino, or tetrazolyl groups; both unsubstituted and substituted).

The terms "halo" and "halogen" refer to any radical of fluorine, chlorine, bromine or iodine.

The terms "ring" and "ring system" refer to a ring comprising the delineated number of atoms, said atoms being carbon or, where indicated, a heteroatom such as nitrogen, oxygen or sulfur. The ring itself, as well as any substituents thereon, can be attached at any atom that allows a stable compound to be formed.

The term "aryl" refers to an aromatic 5-8 membered monocyclic, 8-12 membered bicyclic, or 11-14 membered tricyclic ring system wherein 0, 1, 2, or 3 atoms of each ring can be substituted by a substituent. Examples of aryl groups include phenyl, naphthyl and the like.

The term "heteroaryl" refers to an aromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, wherein 0, 1, 2 or 3 atoms of each ring can be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, wherein 0, 1, 2 or 3 atoms of each ring can be substituted by a substituent. Examples of heterocyclyl groups include piperizinyl, pyrrolidinyl, dioxanyl, morpholinyl, tetrahydrofuranyl, and the like.

Suitable substituents for aryl, heteroaryl, and heterocyclyl groups are the same as the substituents for alkyl groups.

The present invention provides methods of treating and/or preventing pain, e.g., neuropathic pain, in a subject, comprising administering to a subject in need thereof certain compounds encompassing both spicamycin and spicamycin derivatives and pharmaceutically acceptable salts, prodrugs, and optical isomers thereof. Numerous spicamycin derivatives are known in the art (see, e.g., U.S. Pat. Nos. 5,461,036, 5,631,238, 5,905,069, 7,196,071, and 7,375,094, each incorporated herein by reference in its entirety). Also provided are pharmaceutical compositions comprising one or more compounds that are spicamycin derivatives. In some embodiments, the pharmaceutical compositions are formulated to cause fewer side effects (e.g., gastrointestinal irritation, nausea, vomiting, and/or diarrhea) than pharmaceutical compositions of spicamycin derivatives known in the art. For example, the formulation described in Example 2 is expected to produce fewer gastrointestinal disturbances. In other embodiments, the compounds are administered at doses that are lower than those used previously in the art (e.g., for the treatment of cancer) yet are effective to treat and/or prevent pain.

Accordingly, as one aspect, the invention provides methods for treating or preventing pain, e.g., neuropathic pain, in a subject, comprising administering to a subject in need thereof, a treatment or prevention effective amount of a compound of Formula II:

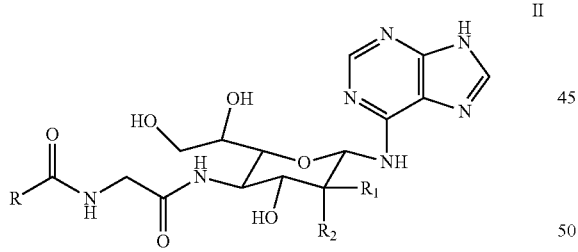

wherein $R_1$ and $R_2$ are different from each other and represent H or OH, and R represents a substituted or unsubstituted alkyl, alkenyl, alkynyl, or cycloalkyl;
or a pharmaceutically acceptable salt, prodrug, or optical isomer thereof.

In some embodiments of the compound of Formula II, R is selected from the group consisting of:
(1) a linear alkenyl having 11-13 carbon atoms;
(2) a linear, unsubstituted alkyl having 11-13 carbon atoms and no double or triple bonds;
(3) a linear haloalkyl having 10-15 carbon atoms;
(4) $CH_3(CH_2)_nCH(OH)$— or $CH_3(CH_2)_{n-1}CH(OH)CH_2$—, wherein n denotes an integer from 9-13;
(5) an alkyl having 10-15 carbon atoms substituted with an azide group or a cyano group;
(6) a linear alkyl having 10-13 carbon atoms substituted with a phenoxy group or a halogen-substituted phenoxy group;

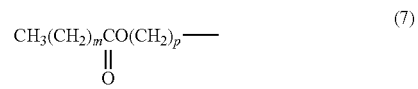

wherein m denotes an integer from 0-2 and p denotes an integer from 9-14;

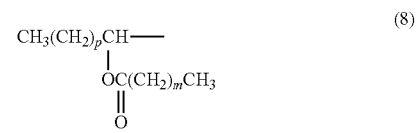

wherein m denotes an integer from 0-2 and p denotes an integer from 8-13;

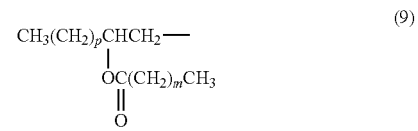

wherein m denotes an integer from 0-2 and p denotes an integer from 10-15;
(10) $CH_3(CH_2)_mSO_2O(CH_2)_p$—, wherein m denotes an integer from 0-3 and p denotes an integer from 9-14;

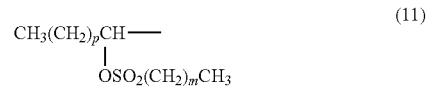

wherein m denotes an integer from 0-3 and p denotes an integer from 10-15;

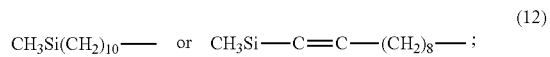

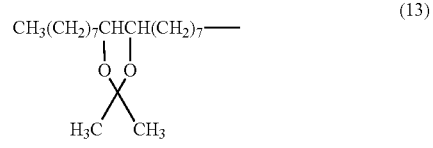

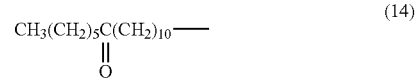

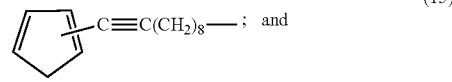

(16) a linear alkadienyl having 11-13 carbon atoms.

In other embodiments of the compound of Formula II, R is selected from the group consisting of:
(1) a linear alkenyl having 11-13 carbon atoms;
(2) a linear, unsubstituted alkyl having 11-13 carbon atoms and no double or triple bonds; and (3) CH$_3$(CH$_2$)$_n$CH(OH)— or CH$_3$(CH$_2$)$_n$CH(OH)CH$_2$—, wherein n denotes an integer from 9-13.

In other embodiments of the compound of Formula II, R is an alkadienyl having 11, 12, or 13 carbon atoms.

In certain embodiments of the compound of Formula II, R$_1$ is H and R$_2$ is OH. In other embodiments, R$_1$ is H and R$_2$ is OH. In still other embodiments, R$_1$ and R$_2$ are both H or both OH.

In one embodiment, the compound of Formula II is 6-[4-deoxy-4-[(2E,4E)-tetradecadienoylglycyl}amino-L-glycero-β-L-mannoheptopyranosyl]amino-9H-purine (KRN5500), having the structure shown below:

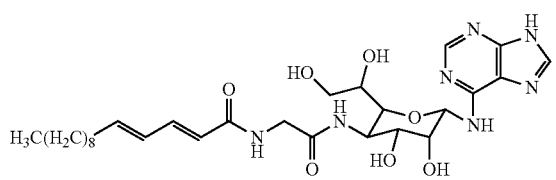

or a pharmaceutically acceptable salt, prodrug, or optical isomer thereof.

Various spicamycin derivatives corresponding to Formula II have been synthesized that vary in the specific R$_1$, R$_2$, and R groups (see, e.g., U.S. Pat. Nos. 5,461,036, 5,631,238, and 5,905,069 and U.S. Patent Publication No. 2004/0038927 A1) and are encompassed by the present invention. Exemplary compounds include the following compounds as well as pharmaceutically acceptable salts, prodrugs, and optical isomers thereof:

6-[4'-N—(N'-tridecanoylglycyl)spicaminyl-amino]purine (SPM 9),
6-[4'-N—(N'-tetradecanoylglycyl)spicaminyl-amino]purine (SPM 10),
6-[4'-N—(N'-10-methylundecanoylglycyl)spicaminyl-amino]purine (SPK 9),
6-[4'-N—(N'-11-methyldodecanoylglycyl)spicaminyl-amino]purine (SPK 251),
6-[4'-N—(N'-12-methyltridecanoylglycyl)spicaminyl-amino]purine (SPK 136),
6-[4'-N—(N'-11-dodecenoylglycyl)spicaminyl-amino]purine (SPK 44),
6-[4'-N—(N'-12-tridecenoylglycyl)spicaminyl-amino]purine (SPK 142),
6-[4'-N—(N'-cis-9-tetradecenoylglycyl)spicaminyl-amino]purine (SPK 231),
6-[4'-N—(N'-cis-9-hexadecenoylglycyl)spicaminyl-amino]purine (SPK 148),
6-[4'-N—(N'-trans-2-dodecenoylglycyl)spicaminyl-amino]purine (SPK 86),
6-[4'-N—(N'-trans-2-tetradecenoylglycyl)spicaminyl-amino]purine (SPK 156),
6-[4'-N—(N'-trans-2-hexadecenoylglycyl)spicaminyl-amino]purine (SPK 188),
6-[4'-N—(N'-trans,trans-2,4-dodecadienoyl-glycyl)spicaminyl-amino]purine (SPK 282),
6-[4'-N—(N'-trans,trans-2,4-tridecadienoyl-glycyl) spicaminyl-amino]purine (SPK 281),
6-[4'-N—(N'-trans,trans-2,4-tetradecadienoyl-glycyl) spicaminyl-amino]purine (SPK 241),
6-[4'-N—(N'-11-bromoundecanoylglycyl)spicaminyl-amino]purine (SPK 64),
6-[4'-N—(N'-12-bromododecanoylglycyl)spicaminyl-amino]purine (SPK 152),
6-[4'-N—(N'-13-bromotridecanoylglycyl)spicaminyl-amino]purine (SPK 276),
6-[4'-N—(N'-14-bromotetradecanoylglycyl)spicaminyl-amino]purine (SPK 273),
6-[4'-N—(N'-12-chlorododecanoylglycyl)spicaminyl-amino]purine (SPK 132),
6-[4'-N—(N'-13-chlorotridecanoylglycyl)spicaminyl-amino]purine (SPK 278),
6-[4'-N—(N'-14-chlorotetradecanoylglycyl)spicaminyl-amino]purine (SPK 280),
6-[4'-N—(N'-14-fluorotetradecanoylglycyl)spicaminyl-amino]purine (SPK 279),
6-[4'-N—(N'-15-fluoropentadecanoylglycyl)spicaminyl-amino]purine (SPK 247),
6-[4'-N—(N'-16-fluorohexadecanoylglycyl)spicaminyl-amino]purine (SPK 157),
6-[4'-N—(N'-11-iodoundecanoylglycyl)spicaminyl-amino]purine (SPK 165),
6-[4'-N—(N'-2-chlorohexadecanoylglycyl)spicaminyl-amino]purine (SPK 135),
6-[4'-N—(N'-2-fluorododecanoylglycyl)spicaminyl-amino]purine (SPK 159),
6-[4'-N—(N'-2-fluorohexadecanoylglycyl)spicaminyl-amino]purine (SPK 233),
6-[4'-N—(N'-2,2-difluorotetradecanoylglycyl)-spicaminyl-amino]purine (SPK 182),
6-[4'-N—(N'-2-hydroxyhexadecanoylglycyl)spicaminyl-amino]purine (SPK 112),
6-[4'-N—(N'—(S)-2-hydroxyhexadecanoylglycyl)-spicaminyl-amino]purine (SPK 271),
6-[4'-N—(N'—(R)-3-hydroxytetradecanoylglycyl)-spicaminyl-amino]purine (SPK 270),
6-[4'-N—(N'—(S)-3-hydroxytetradecanoylglycyl)-spicaminyl-amino]purine (SPK 274),
6-[4'-N—(N'-3-hydroxyhexadecanoylglycyl)-spicaminyl-amino]purine (SPK 115),
6-[4'-N—(N'-16-cyanohexadecanoylglycyl)-spicaminyl-amino]purine (SPK 177),
6-[4'-N—(N'-11-phenoxyundecanoylglycyl)-spicaminyl-amino]purine (SPK 422),
6-[4'-N—(N'-12-phenoxydodecanoylglycyl)-spicaminyl-amino]purine (SPK 249),
6-[4'-N—(N'—(R)-2-acetoxyhexadecanoylglycyl)-spicaminyl-amino]purine (SPK 198),
6-[4'-N—(N'-3-acetoxyhexadecanoylglycyl)-spicaminyl-amino]purine (SPK 189),
6-[4'-N—(N'-12-butanesulfonyloxydodecanoylglycyl)-spicaminyl-amino]purine (SPK 232),
6-{4'-N—[N'-11-(2'-thienyl)-10-undecynoylglycyl]-spicaminyl-amino}purine (SPK 262),
6-{4'-N—[N'-11-(3'-thienyl)-10-undecynoylglycyl]-spicaminyl-amino}purine (SPK 263), and
6-{4'-N—[N'-11-(3'-furyl)-10-undecynoylglycyl]-spicaminyl-amino}purine (SPK 266).

Compounds of Formula II can be synthesized using art-known methods, e.g., as disclosed in U.S. Pat. Nos. 5,631, 238, 5,461,036, and 5,905,069.

The invention also provides methods for treating or preventing pain, e.g., neuropathic pain, in a subject, comprising administering to a subject in need thereof, a treatment or prevention effective amount of a compound of Formula

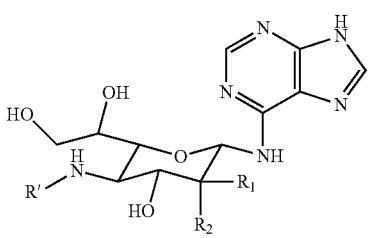

III wherein $R_1$ and $R_2$ are different from each other and represent H or OH, and R' represents (1) a substituted or unsubstituted alkyl or alkenyl having one or two carbon atoms, or (2) H;

or a pharmaceutically acceptable salt, prodrug, or optical isomer thereof.

In one embodiment of the compound of Formula III, R' is a substituted alkyl. In another embodiment, R' has two carbons. In a further embodiment, R' comprises a peptide bond. In yet another embodiment, R' comprises an amino group, e.g., a primary amino group. In one embodiment, R' is —COCH$_2$NH$_2$.

In one embodiment of the compound of Formula III, $R_1$ is H and $R_2$ is OH (the compound known as 4'-N-glycyl spicamycin amino nucleoside (SAN-Gly)). In another embodiment, R' is H, $R_1$ is H and $R_2$ is OH (the compound known as SAN). See, e.g., Kamishohara et al., *Oncology Res.* 6:383 (1994).

As yet a further aspect, the invention provides methods for treating or preventing pain, e.g., neuropathic pain, in a subject, comprising administering to a subject in need thereof, a treatment or prevention effective amount of a compound of Formula IV:

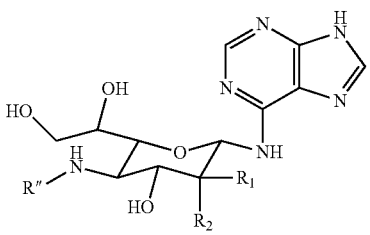

IV wherein $R_1$ and $R_2$ are different from each other and represent H or OH, each R" group is independently H or an alkyl, alkenyl, alkynyl, or cycloalkyl group having 1 to 5 carbon atoms substituted with 1 to 3 independent $R^3$ or $R^4$;

each $R^3$ is independently heterocyclyl or heteroaryl, either optionally substituted with 1-3 independent $R^5$;

each $R^4$ is independently halogen, oxygen, sulfur, CF$_3$, SR$^6$, OR$^6$, OC(O)R$^6$, NR$^6$R$^6$, NR$^6$R$^7$, COOR$^6$, C(O)R$^6$, or C(O)NR$^6$R$^6$;

each $R^5$ is independently C$_1$-C$_{10}$ alkyl; C$_2$-C$_{10}$ alkenyl; C$_2$-C$_{30}$ alkynyl; C$_3$-C$_{10}$ cycloalkyl; halo; haloalkyl; SR$^6$; OR$^6$; NR$^6$R$^6$; COOR$^6$; NO$_2$; CN; C(O)R$^6$; C(O)NR$^6$R$^6$; OC(O)R$^6$; S(O)$_2$R$^6$; S(O)$_2$NR$^6$R$^6$; NR$^6$C(O)NR$^6$R$^6$; NR$^6$C(O)R$^6$; NR$^6$(COOR$^6$); NR$^6$C(O)R$^8$; NR$^6$S(O)$_2$NR$^6$R$^6$; NR$^6$S(O)$_2$R$^6$; NR$^6$S(O)$_2$R$^8$; or C$_1$-C$_{10}$ alkyl; C$_2$-C$_{10}$ alkenyl; C$_2$-C$_{10}$ alkynyl; or C$_3$-C$_{10}$ cycloalkyl substituted with R$^4$ or R$^8$;

each $R^6$ is independently H, C$_1$-C$_{10}$ alkyl; C$_2$-C$_{10}$ alkenyl; C$_2$-C$_{10}$ alkynyl; C$_3$-C$_{10}$ cycloalkyl; R$^8$; or C$_1$-C$_{10}$ alkyl; C$_2$-C$_{10}$ alkenyl; C$_2$-C$_{10}$ alkynyl; or C$_3$-C$_{10}$ cycloalkyl substituted with R$^8$;

each $R^7$ is independently COOR$^9$, C(O)NR$^9$R$^9$, S(O)$_2$R$^9$; or S(O)$_2$NR$^9$R$^9$;

each $R^8$ is independently aryl, heteroaryl, or heterocyclyl; and each $R^9$ is independently H, C$_1$-C$_{10}$ alkyl, C$_2$-C$_{10}$ alkenyl, C$_2$-C$_{10}$ alkynyl, C$_3$-C$_{10}$ cycloalkyl, aryl, heteroaryl, or heterocyclyl;

or a pharmaceutically acceptable salt, prodrug, or optical isomer thereof.

In one embodiment of the compound of Formula IV, $R_1$ and $R_2$ are different from each other and represent H or OH, and R" represents (1) a substituted or unsubstituted alkyl or alkenyl having one or two carbon atoms, or (2) H. In another embodiment, each R" group can independently be an H or alkyl or alkenyl group having 1 to 2 carbon atoms substituted with 1 to 3 independent $R^3$ or $R^4$.

Compounds of Formula III and IV can be prepared using methods known in the art. For example, general synthetic strategies are described in U.S. Pat. Nos. 5,461,036, 5,631,238, 5,905,069, 7,196,071, and 7,375,094. These strategies can be adapted to attach any R' or R" group containing one or two carbons onto a sugar group, as shown in Formula III and IV. A specific semi-synthetic strategy for preparing SAN and SAN-Gly is described in Kamishohara et al., *J. Antibiotics* 46:1439 (1993); Kamishohara et al., *Oncology Res.* 6:383 (1994); and U.S. Pat. Nos. 5,461,036 and 5,631,238.

The compounds of this invention include all pharmaceutically acceptable salt forms thereof. Examples of such salts include those derived from pharmaceutically acceptable inorganic and organic acids and bases. Examples of suitable acid salts include, without limitation, acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, hydroxynapthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds of the invention and their pharmaceutically acceptable acid addition salts.

Salts derived from appropriate bases include, without limitation, alkali metal (e.g., sodium, potassium), alkaline earth metal (e.g., magnesium and calcium), ammonium and N-(alkyl)$_4$$^+$ salts.

Compounds of the formulae herein include those having quaternization of any basic nitrogen-containing group therein.

The discussion herein is, for simplicity, provided without reference to stereoisomerism. Those skilled in the art will appreciate that the compounds of Formula I, II, III, and IV can contain one or more asymmetric centers and thus occur as racemates and racemic mixtures, single optical isomers, individual diastereomers, and diastereomeric mixtures. All such isomeric forms of these compounds are expressly included in the present invention.

Similarly, compounds of the invention containing a double bond can exist in the form of geometric isomers, which can be readily separated and recovered by conventional procedures. Such isomeric forms are included in the scope of this invention.

Further, the compounds of the invention include prodrugs of the compounds of Formula I, II, III, and IV that are converted to the active compound in vivo. For example, the compound can be modified to enhance cellular permeability (e.g., by esterification of polar groups) and then converted by cellular enzymes to produce the active agent. Methods of masking charged or reactive moieties as a pro-drug are known by those skilled in the art (see, e.g., P. Korgsgaard-Larsen and H. Bundgaard, A Textbook of Drug Design and Development, Reading U.K., Harwood Academic Publishers, 1991).

The term "prodrug" refers to compounds that are rapidly transformed in vivo to yield the parent compound of the above formula, for example, by hydrolysis in blood, see, e.g., T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Exemplary prodrugs include a prodrug that is metabolized in vivo by a subject to an active drug having an activity of the compounds as described herein, wherein the prodrug is an ester of an alcohol or carboxylic acid group, if such a group is present in the compound; an amide of an amine group or carboxylic acid group, if such groups are present in the compound; a urethane of an amine group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described, for example, in U.S. Pat. No. 6,680,324 and U.S. Pat. No. 6,680,322.

The term "pharmaceutically acceptable prodrug" (and like terms) as used herein refers to those prodrugs of the compounds of the present invention which are, within the scope of sound medical judgment, suitable for use in contact with the tissues of humans and/or other animals without undue toxicity, irritation, allergic response and the like, commensurate with a reasonable risk/benefit ratio, and effective for their intended use, as well as the zwitterionic forms, where possible, of the compounds of the invention.

In one aspect of the invention, spicamycin derivatives are used to treat or prevent pain in a subject. The pain can be due to a neuropathy, e.g., neuropathic pain. The neuropathy can be any form of neuropathy. In some embodiments, the neuropathy is selected from the group consisting of chemotherapy-induced neuropathy, cancer-related neuropathy, HIV-related peripheral neuropathy, post-herpetic neuralgia, diabetic neuropathy, sciatica, fibromyalgia, chronic fatigue syndrome pain, multiple sclerosis pain, complex regional pain syndrome type I, complex regional pain syndrome type II, central pain syndrome, painful traumatic mononeuropathy, post surgical pain syndrome, post mastectomy syndrome, post thoracotomy syndrome, phantom pain, nerve root avulsion, post radiation neuropathy, repetitive movement nerve injury, repetitive stress injury, and post injury neuropathy. In one embodiment, the pain that is treated or prevented includes nociceptive pain. In another embodiment, the pain that is treated or prevented excludes nociceptive pain.

In one embodiment of the invention, the spicamycin derivative is administered to the subject as needed to treat or prevent pain. The spicamycin derivative can be administered continuously or intermittently. In one embodiment, the spicamycin derivative is administered to the subject more than once a day or once every 1, 2, 3, 4, 5, 6, or 7 days. In another embodiment, the spicamycin derivative is administered to the subject no more than once a week, e.g., no more than once every two weeks, once a month, once every two months, once every three months, once every four months, once every five months, once every six months, or longer. In a further embodiment, the spicamycin derivative is administered using two or more different schedules, e.g., more frequently initially (for example to build up to a certain level, e.g., once a day or more) and then less frequently (e.g., once a week or less). The spicamycin derivative can be administered 1 hour, 2 hours, 3 hours, 4 hours, 5 hours, 6 hours, 12 hours, 1 day, 2 days, 3 days, 4 days, 5 days, 6 days, 1 week, 2 weeks, 3 weeks, 4 weeks, or more prior to the onset of pain (e.g., prior to an event that is likely to induce pain). The compound can be administered 1 hour, 2 hours, 3 hours, 4 hours, 5 hours, 6 hours, 12 hours, 1 day, 2 days, 3 days, 4 days, 5 days, 6 days, 1 week, 2 weeks, 3 weeks, 4 weeks, or more after the onset of pain or an event likely to induce pain. In other embodiments, the spicamycin derivative can be administered by any discontinuous administration regimen. In one example, the compound can be administered not more than once every three days, every four days, every five days, every six days, every seven days, every eight days, every nine days, or every ten days, or longer. The administration can continue for one, two, three, or four weeks or one, two, or three months, or longer. Optionally, after a period of rest, the compound can be administered under the same or a different schedule. The period of rest can be one, two, three, or four weeks, or longer, according to the pharmacodynamic effects of the compound on the subject.

The spicamycin derivative can be delivered to the subject by any suitable route, e.g., oral, rectal, buccal (e.g., sublingual), vaginal, parenteral (e.g., subcutaneous, intramuscular, intradermal, or intravenous), topical (i.e., both skin and mucosal surfaces, including airway surfaces) and transdermal administration. In one embodiment, the route is intravenous. In another embodiment, the route is subcutaneous. In another embodiment, the route is intramuscular. The spicamycin derivative is delivered to the subject at a dose that is effective to treat and/or prevent the pain. The effective dosage will depend on many factors including the gender, age, weight, and general physical condition of the subject, the severity of the pain, the particular compound or composition being administered, the duration of the treatment, the nature of any concurrent treatment, the carrier used, and like factors within the knowledge and expertise of those skilled in the art. As appropriate, a treatment effective amount in any individual case can be determined by one of ordinary skill in the art by reference to the pertinent texts and literature and/or by using routine experimentation (see, e.g., Remington, *The Science and Practice of Pharmacy* ($21^{st}$ ed. 2005)). In one embodiment, the spicamycin derivative is administered at a dose of about 0.2 to about 10.0 mg/m$^2$, e.g., about 0.6 to about 4.0 mg/m$^2$, about 1.0 to about 3.0 mg/m$^2$, or about 0.6, 0.8, 1.0, 1.2, 1.4, 1.6, 1.8, 2.0, 2.2, 2.4, 2.6, 2.8, 3.0, 3.2, 3.4, 3.6, 3.8, or 4.0 mg/m$^2$. In some instances, the dose can be even lower, e.g., as low as 0.1, 0.05. 0.01. 0.005, or 0.001 mg/m$^2$ or lower. In some instances, the dose can be even higher, e.g., as high as 20, 50, 100, 500, or 1000 mg/m$^2$ or higher. The present invention encompasses every sub-range within the cited ranges and amounts.

In one embodiment of the invention, the subject is one that has developed a neuropathy and the compound is administered to the subject after the development of neuropathy in order to treat the pain. In another embodiment, the subject is one that has not developed a neuropathy and the compound is administered to the subject to prevent the occurrence of pain. In one embodiment, the subject is one that is undergoing an event that is likely to result in the development of neuropathy. The spicamycin derivative can be delivered to the subject prior to the event occurring, concurrently with the event, and/or after the event occurs but before the development of pain. Events that are likely to result in the development of neuropathy are well known and include, without limitation, surgery (e.g., amputation, mastectomy, thoracotomy), traumatic nerve damage, radiation treatment, and chemotherapy.

In one embodiment of the invention, the subject is currently undergoing, will be undergoing, and/or has undergone chemotherapy treatment with one or more chemotherapeutic agents that are known or suspected to induce neuropathy and the spicamycin derivative is administered to prevent and/or treat pain. Chemotherapeutic agents known to induce neuropathy include, without limitation, vinca alkaloids (e.g., vinblastine, vincristine, vindesine, or vinorelbine), taxanes (e.g., paclitaxel or docetaxel), platinum-based compounds (e.g., cisplatin, carboplatin, nedaplatin, triplatin tetranitrate, satraplatin, or oxaliplaten), and VELCADE (bortezomib).

In one aspect of the invention, the spicamycin derivative is delivered to a subject concurrently with a further agent. The further agent can be delivered in the same composition as the spicamycin derivative or in a separate composition. The further agent can be delivered to the subject on a different schedule or by a different route as compared to the spicamycin derivative. The further agent can be any agent that provides a benefit to the subject. Further agents include, without limitation, chemotherapeutic agents, antiemetic agents, analgesic agents (e.g., opioids and/or systemic local anesthetics), anti-inflammatory agents, and peroxisome proliferator-activated receptor (PPAR) agonists, e.g., PPAR δ agonists.

Examples of chemotherapeutic agents include, without limitation, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacytidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, hydroxyurea, idarubicin hydrochloride, ifosfarnide, ilmofosine, interleukin II (including recombinant interleukin II or rIL2), interferon alfa-2a, interferon alfa-2b, interferon alfa-n1, interferon alfa-n3, interferon beta-Ia, interferon gamma-Ib, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozotocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other chemotherapeutic agents include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; prostatic carcinoma antiandrogen; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat;

imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; odansteron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of antiemetic agents include, without limitation, metoclopromide, domperidone, prochlorperazine, promethazine, chlorpromazine, trimethobenzamide, odansteron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, and mixtures thereof.

Examples of analgesic agents include, without limitation, the opioids allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, and tramadol.

Examples of anti-inflammatory agents include, without limitation, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, celecoxib, rofecoxib, and corticosteroids (e.g., prednisone, methylprednisolone, dexamethasone).

Examples of PPAR δ agonists include, without limitation, those disclosed in U.S. Pat. Nos. 6,713,514, 6,677,298, 6,462,046, 5,925,657, 5,326,770 EP 1586573, U.S. 20050245589, and WO 2005049572 and in Combs et al., *J. Neurosci.* 20:558 (2000), including without limitation GW 501516, GW 0742, L-165041, and carbaprostacyclin.

The present invention finds use in research as well as veterinary and medical applications. Suitable subjects are generally mammalian subjects. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects.

In particular embodiments, the subject is a human subject that has pain (e.g., neuropathic pain and/or nociceptive pain and/or non-neuropathic inflammatory pain) and/or is anticipated to experience pain. In other embodiments, the subject used in the methods of the invention is an animal model of pain.

The subject can be a subject "in need of" the methods of the present invention, e.g., in need of the therapeutic and/or prophylactic effects of the inventive methods. For example, the subject can be a subject that is experiencing pain (e.g., neuropathic pain and/or nociceptive pain and/or non-neuropathic inflammatory pain) and/or is anticipated to experience pain, and the methods and compositions of the invention are used for therapeutic and/or prophylactic treatment.

The subject can further be a laboratory animal, e.g., an animal model of pain (see, e.g., Kim et al., *Pain* 50:355 (1992); Bennett et al., *Pain* 33:87 (1988); U.S. Patent Publication 2004/0038927).

The spicamycin derivatives described above can be formulated for administration in a pharmaceutical carrier in accordance with known techniques. See, e.g., Remington, *The Science And Practice of Pharmacy* ($21^{st}$ ed. 2005). In the manufacture of a pharmaceutical formulation according to the invention, the compound is typically admixed with, inter alia, an acceptable carrier. The carrier must, of course, be acceptable in the sense of being compatible with any other ingredients in the formulation and must not be deleterious to the patient. The carrier can be a solid or a liquid, or both, and can be formulated with the compound as a unit-dose formulation, for example, a tablet, which can contain from 0.01% or 0.5% to 95% or 99% by weight of the compound. One or more compounds can be incorporated in the formulations of the invention, which can be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration can be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations can be prepared by any suitable method of pharmacy which includes the step of bringing into association the compound and a suitable carrier (which can contain one or more accessory ingredients as noted above). In general, the formulations of the invention are prepared by uniformly and intimately admixing the compound with a liquid or finely divided solid carrier, or both, and then, if necessary, shaping the resulting mixture. For example, a tablet can be prepared by compressing or molding a powder or granules containing the compound, optionally with one or more accessory ingredients. Compressed tablets can be prepared by compressing, in a suitable machine, the compound in a free-flowing form, such as a powder or granules optionally mixed with a binder, lubricant, inert diluent, and/or surface active/dispersing agent(s). Molded tablets can be made by molding, in a suitable machine, the powdered compound moistened with an inert liquid binder.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit\dose (e.g., in a syringe or other injection device) or multi-dose containers, for example sealed ampoules and vials, and can be stored in a freeze-dried (lyophilized) condition requiring only the addition of the sterile liquid carrier, for example, saline or water-for-injection immediately prior to use. Extemporaneous injection solutions and suspensions can be prepared from sterile powders, granules and tablets of the kind previously described. For example, in one aspect of the present invention, there is provided an injectable, stable, sterile composition comprising one or more compounds, in a unit dosage form in a sealed container. The compound is provided in the form of a lyophilizate which is capable of being reconstituted with a suitable pharmaceutically acceptable carrier to form a liquid composition suitable for injection thereof into a subject. The unit dosage form typically comprises from about 1 mg to about 10 grams of the compound. When the compound is substantially water-insoluble (e.g., when conjugated to a lipid), a sufficient amount of emulsifying agent which is physiologically acceptable can be employed in sufficient quantity to emulsify the compound in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharm. Res.* 3:318 (1986)) and typically take the form of an optionally buffered aqueous solution of the compound. Suitable formulations comprise citrate or bis\tris buffer (pH 6) or ethanol/water and contain from 0.1 to 0.2 M active ingredient.

Other pharmaceutical compositions can be prepared from the compounds disclosed herein, such as aqueous base emulsions. In such an instance, the composition will contain a sufficient amount of pharmaceutically acceptable emulsifying agent to emulsify the desired amount of the compound. Particularly useful emulsifying agents include phosphatidyl cholines and lecithin.

In addition to compound, the pharmaceutical compositions can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions can contain microbial preservatives. Useful microbial preservatives include methylparaben, propylparaben, and benzyl alcohol. The microbial preservative is typically employed when the formulation is placed in a vial designed for multidose use. Other additives that are well known in the art include, e.g., detackifiers, anti-foaming agents, antioxidants (e.g., ascorbyl palmitate, butyl hydroxy anisole (BHA), butyl hydroxy toluene (BHT) and tocopherols, e.g., α-tocopherol (vitamin E)), preservatives, chelating agents (e.g., EDTA and/or EGTA), viscomodulators, tonicifiers (e.g., a sugar such as sucrose, lactose, and/or mannitol), flavorants, colorants, odorants, opacifiers, suspending agents, binders, fillers, plasticizers, lubricants, and mixtures thereof. The amounts of such additives can be readily determined by one skilled in the art, according to the particular properties desired.

The additive can also comprise a thickening agent. Suitable thickening agents can be those known and employed in the art, including, e.g., pharmaceutically acceptable polymeric materials and inorganic thickening agents. Exemplary thickening agents for use in the present pharmaceutical compositions include polyacrylate and polyacrylate co-polymer resins, for example poly-acrylic acid and poly-acrylic acid/methacrylic acid resins; celluloses and cellulose derivatives including: alkyl celluloses, e.g., methyl-, ethyl- and propyl-celluloses; hydroxyalkyl-celluloses, e.g., hydroxypropyl-celluloses and hydroxypropylalkyl-celluloses such as hydroxypropyl-methyl-celluloses; acylated celluloses, e.g., cellulose-acetates, cellulose-acetatephthallates, cellulose-acetatesuccinates and hydroxypropylmethyl-cellulose phthalates; and salts thereof such as sodium-carboxymethyl-celluloses; polyvinylpyrrolidones, including for example poly-N-vinylpyrrolidones and vinylpyrrolidone co-polymers such as vinylpyrrolidone-vinylacetate co-polymers; polyvinyl resins, e.g., including polyvinylacetates and alcohols, as well as other polymeric materials including gum traganth, gum arabicum, alginates, e.g., alginic acid, and salts thereof, e.g., sodium alginates; and inorganic thickening agents such as atapulgite, bentonite and silicates including hydrophilic silicon dioxide products, e.g., alkylated (for example methylated) silica gels, in particular colloidal silicon dioxide products. Such thickening agents as described above can be included, e.g., to provide a sustained release effect. However, where oral administration is intended, the use of thickening agents as aforesaid will generally not be required and is generally less preferred. Use of thickening agents is, on the other hand, indicated, e.g., where topical application is foreseen.

In one embodiment, the pharmaceutical compositions of the invention comprise nanoparticles or nanostructures. These small scale carriers (generally less than 1 micron in diameter) provide improved drug delivery by several means, including prolonging circulation in the blood; enhancing water or lipid solubility; responding to local stimuli, such as changes in pH, temperature, or light; penetrating anatomical features such as cell walls, blood vessels, stomach epithelium, and blood-brain barrier; and selectively targeting specific cell types. Several classes of nanoparticles have been developed, including nanoemulsions, liposomes, carbon fullerenes and nanotubes, ceramic nanoparticles (derived from silicon, titanium, and aluminum), metallic particles (iron oxide and gold- and silver-coated particles) and polymers. The nanoparticles of the compounds of the present invention have an effective average particle size of less than about 2 microns, e.g., less than about 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 250 nm, 200 nm, 150 nm, 100 nm, 75 nm, 50 nm, 25 nm, or 10 nm, as measured by light-scattering methods, microscopy, or other appropriate methods well known to those of ordinary skill in the art.

The pharmaceutical compositions comprising spicamycin derivatives can be in the form of nanoemulsions. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in U.S. Patent Application Nos. 2002/0045667 and 2004/0043041, and U.S. Pat. Nos. 6,015,832, 6,506,803, 6,635,676, and 6,559,189, each of which is incorporated herein by reference in its entirety.

Suitable oils for use in nanoemulsions include, without limitation, soybean oil, avocado oil, squalene oil, olive oil, canola oil, corn oil, rapeseed oil, safflower oil, sunflower oil, fish oils, cinnamon bark, coconut oil, cottonseed oil, flaxseed oil, pine needle oil, silicon oil, mineral oil, essential oil, flavor oils, water insoluble vitamins, and combinations comprising one or more of the foregoing oils.

Suitable solvents for nanoemulsions include, without limitation, an alcohol (e.g., including, but not limited to, methanol, ethanol, propanol, and octanol), glycerol, polyethylene glycol, and an organic phosphate based solvent.

Suitable surfactants include, without limitation, a variety of ionic and nonionic surfactants, as well as other emulsifiers capable of promoting the formation of nanoemulsions. Surfactants that allow the oil phase to remain suspended in the water phase can be used. Both hydrophilic and hydrophobic surfactants can be used. In one embodiment, the nanoemulsion comprises a non-ionic surfactant such as a polysorbate surfactant, i.e., polyoxyethylene ether. Other useful surfactants include, but are not limited to, the polysorbate detergents sold under the tradenames TWEEN 20, TWEEN 40, TWEEN 60, TWEEN 80, phenoxypolyethoxyethanols and polymers thereof, such as TRITON (i.e., X-100, X-301, X-165, X-102, X-200), POLOXAMER 407, Spans (20, 40, 60, and 80), tyloxapol, and combinations comprising one or more of the foregoing surfactants. Additional appropriate surfactants include BRIJ 30, BRIJ 35, BRIJ 52, BRIJ 56, BRIJ 58, BRIJ 72, BRIJ 76, BRIJ 78, BRIJ 92, BRIJ 97, BRIJ 98, and BRIJ 700. Anionic surfactants include, but are not limited to, sodium dodecyl sulfate (SDS). Mixtures of surfactants are also contemplated.

In certain embodiments, the nanoemulsion comprises particles of an average diameter less than about 1000 nm, e.g., less than about 500, 250, 200, 150, 100, or 50 nm. Emulsion particle size can be determined using any means known in the art, such as, for example, using laser light scattering.

A nanoemulsion composition can contain about 5 to about 90 percent by volume (vol %) of aqueous phase. As used herein, percent by volume (vol %) is based on the total volume of an emulsion or nanoemulsion. In one embodiment, the aqueous phase is about 5 to about 50 vol %. In one embodiment, the aqueous phase is about 10 to about 40 vol %. In another embodiment, the aqueous phase is about 15 to about 30 vol %. In a further embodiment, the aqueous phase is about 5, 10, 15, 20, 25, 30, 35, 40, 45, 50, 55, 60, 65, 70, 75, 80, 85, or 90 vol % or any range therein. The aqueous phase ranges from a pH of about 4 to about 10. In one embodiment the pH of the aqueous phase ranges from about 6 to about 8. In another embodiment, the pH of the aqueous phase is about 4.0, 4.5, 5.0, 5.5, 6.0, 6.5, 7.0, 7.5, 8.0, 8.5, 9.0, 9.5, or 10.0. The pH of the aqueous phase can be adjusted by addition of an acid or a base such as, for example, hydrochloric acid or sodium hydroxide. In one embodiment, the aqueous phase is deionized water or distilled water.

The oil phase of a nanoemulsion can contain one or more oils and/or one or more organic solvents. The oil phase of a nanoemulsion contains about 30 to about 90 vol % oil, based on the total volume of the nanoemulsion. In one embodiment, the nanoemulsion contains about 60 to about 80 vol % oil. In another embodiment, the nanoemulsion contains about 60 to about 70 vol % oil. In a further embodiment, the oil phase is about 30, 35, 40, 45, 50, 55, 60, 65, 70, 75, 80, 85, or 90 vol % or any range therein. The oil phase also contains from about 3 to about 25 vol % of an organic solvent based on the total volume of the nanoemulsion. In one embodiment, the nanoemulsion contains about 5 to about 10 vol % of an organic solvent. In another embodiment, the organic solvent is about 3, 4, 5, 6, 7, 8, 9, 10, 11, 12, 13, 14, 15, 16, 17, 18, 19, 20, 21, 22, 23, 24, or 25 vol % or any range therein.

A nanoemulsion can contain about 3 to about 25 vol % of one or more surfactants, based on the total volume of nanoemulsion. In one embodiment, the nanoemulsion contains about 5 to about 10 vol % of one or more surfactants. In another embodiment, the one or more surfactants is about 3, 4, 5, 6, 7, 8, 9, 10, 11, 12, 13, 14, 15, 16, 17, 18, 19, 20, 21, 22, 23, 24, or 25 vol % or any range therein.

In one particular embodiment, the nanoemulsion comprises about 5 to about 25 weight % of an oil phase, e.g., about 5 to about 15 weight %, e.g., about 5, 6, 7, 8, 9, 10, 11, 12, 13, 14, 15, 16, 17, 18, 19, 20, 21, 22, 23, 24, or 25 weight %. In one embodiment, the oil phase comprises two or more components, e.g., an oil and a fractionated oil. In a particular embodiment, the oil phase comprises soybean oil and fractionated palm oil (e.g., MIGLYOL 812). In a further embodiment, the oil phase comprises, consists essentially of, or consists of about 7 weight % soybean oil and about 7 weight % MIGLYOL 812.

In one particular embodiment, the nanoemulsion comprises about 3 to about 20 weight % of one or more surfactants, e.g., about 5 to about 15 weight %, e.g., about 3, 4, 5, 6, 7, 8, 9, 10, 11, 12, 13, 14, 15, 16, 17, 18, 19, or 20 weight %. In one embodiment, the nanoemulsion comprises two or more surfactants. In a particular embodiment, the nanoemulsion comprise soy lecithin and sodium oleate, e.g., about 7 weight % soy lecithin and about 0.3 weight % sodium oleate.

In one particular embodiment, the nanoemulsion comprises, consists essentially of, or consists of about 10 to about 15 weight % oil phase, about 5 to about 10 weight % surfactant, and about 50 to about 70 weight % aqueous phase. In one embodiment, the nanoemulsion comprises, consists essentially of, or consists of about 13 to about 15 weight % oil phase, about 6 to about 8 weight % surfactant, and about 55 to about 65 weight % aqueous phase. In a further embodiment, the nanoemulsion comprises, consists essentially of, or consists of about 7 weight % soybean oil, about 7 weight % MIGLYOL 812, about 7 weight % soy lecithin, about 0.3 weight % sodium oleate, and about 62 weight % water. In one embodiment, the nanoemulsion comprises additional excipients, such as a chelator (e.g., EDTA and/or EGTA) and/or a tonicity modifier (e.g., a simple sugar such as sucrose, lactose, and/or mannitol. In another embodiment, the nanoemulsion comprises, consists essentially of, or consists of about 7 weight % soybean oil, about 7 weight % MIGLYOL 812, about 7 weight % soy lecithin, about 0.3 weight % sodium oleate, about 0.006 weight % EDTA, about 17 weight % sucrose, and about 62 weight % water. In certain embodiments, the nanoemulsion has a pH of about 5 to about 7, e.g., about 6.2.

Nanoemulsions and compositions containing nanoemulsions can be produced by any suitable means. A nanoemulsion can be formed in the first instance or can be formed from an emulsion having larger particles. Methods for the production of an emulsion by mixing an oil phase with an aqueous phase are well-known. An emulsion can be formed by blending an oil phase with an aqueous phase on a volume-to-volume basis ranging from about 1:9 to about 9:1 or any range therein, e.g., about 1:5 to about 5:1, about 1:4 to about 4:1, about 1:3 to about 3:1, about 1:2 to about 2:1, or about 1:1. In other embodiments, the ratio of oil phase to aqueous phase is about 5:1, 4:1, 3:1, or 2:1. The oil and aqueous phases can be blended using an apparatus capable of producing shear forces sufficient to form an emulsion such as, for example, a French press or a commercial low shear or high shear mixer. In one embodiment, the emulsions are prepared under conditions of high shear to produce an emulsion having a substantially uniform particle size distribution. In one embodiment, a standard emulsion for use in preparing a nanoemulsion composition is comprised of particles having an average diameter of about 500 nm to about 5 μm or more, e.g., about 500 nm to about 1 μm, about 400 nm to about 5 μm, about 400 nm to about 1 μm, about 250 nm to about 5 μm, and about 250 nm to about 1 μm. To obtain the desired pH, the pH of the aqueous phase can be adjusted using an acid such as hydrochloric acid or a base such as sodium hydroxide.

Forming a nanoemulsion from a standard emulsion can be accomplished, for example, by passing the standard emulsion though a microfluidizer (Microfluidics Corp., Newton, Mass.) several times at a pressure sufficient to produce a desired particle size. A microfluidizer is a homogenizer that operates by pumping a fluid stream into an interaction chamber. The interaction chamber contains fixed-geometry microchannels that accelerate the fluid stream, resulting in high turbulence, shear, and cavitation. A H230Z chamber (400 μm) upstream of a H210Z chamber (200 μm) can be used. Other chamber size and configurations (Y or Z) can be used in forming a nanoemulsion using a microfluidizer. During homogenization, a nanoemulsion can be circulated through a heat exchanger coil or otherwise cooled to keep the temperature of the nanoemulsion from increasing significantly. In one embodiment, a standard emulsion is passed though the microfluidizer for two to five passes at a pressure of about 2,000 to about 10,000 psi. In another embodiment, the pressure is from 3,000 to about 4,000 psi. These conditions can vary depending on factors such as standard emulsion particle size, emulsion composition, and desired final particle size.

Another means of forming a nanoemulsion is passage of a standard emulsion through a high pressure homogenizer, like an EmulsiFlex® high pressure homogenizer (Avestin, Inc., Ottawa, Canada). The number of passages through the homogenizer as well as the flow rate will depend on the particle size of the standard emulsion, emulsion composition, and the desired particle size of the resulting nanoemulsion. Operating pressure is independent from flow rate and will remain at the set value over the process time. In one embodiment, the operating pressure is from about 2,500 to about 20,000 psi. As with the microfluidizing method discussed above, a nanoemulsion can be cooled using a heat exchanger or other method and the nanoemulsion can be passed though the homogenizer from about two to about five times. The particle size depends inversely on both the number of passages and on the operating pressure.

In addition to the above described methods, one can produce a nanoemulsion directly, without premixing. The direct use of, for example, either a microfluidizer or a high pressure homogenizer, as described above, can result in a nanoemulsion with the properties discussed above for a nanoemulsion produced from a premixed standard emulsion.

Nanoemulsions can have a consistency ranging from a semi-solid cream to a watery liquid similar to skim milk. Creamy emulsions can be used as is or mixed with water.

A nanoemulsion can be prepared in a diluted or an undiluted form. In one embodiment, a nanoemulsion shows suitable stability in both diluted and undiluted forms. By suitable stability, it is meant that the emulsions do not show any signs of separation (oil phase from aqueous phase) for at least one month, e.g., at least 2, 3, 4, 5, 6, 7, 8, 9, 10, 12, 18, or 24 months. Stability can be measured at room temperature (about 25° C.), refrigerator temperature (about 4° C.), or freezer temperature (about −20° C.). Settling of the diluted emulsions is an acceptable characteristic and does not indicate separation of an oil phase from an aqueous phase. Settling is due to separation of emulsions from its diluent, not an oil phase separating from an aqueous phase. Such settling is readily reversed by simple shaking of the nanoemulsion, while separation of the concentrated emulsions are not reversed by simple mixing, requiring instead re-emulsification. Nanoemulsions can be stored refrigerated or frozen for enhanced stability. In another embodiment, the nanoemulsion can be lyophilized and later redissolved in water or another aqueous solvent to reform the nanoemulsion, e.g., when ready to be used.

Further, the present invention provides liposomal formulations of the compounds disclosed herein. The technology for forming liposomal suspensions is well known in the art. When the compound is in the form of an aqueous-soluble material, using conventional liposome technology, the same can be incorporated into lipid vesicles. In such an instance, due to the water solubility of the compound, the compound will be substantially entrained within the hydrophilic center or core of the liposomes. The lipid layer employed can be of any conventional composition and can either contain cholesterol or can be cholesterol-free. When the compound of interest is water-insoluble, again employing conventional liposome formation technology, the compound can be substantially entrained within the hydrophobic lipid bilayer which forms the structure of the liposome. In either instance, the liposomes which are produced can be reduced in size, as through the use of standard sonication and homogenization techniques. The liposomal formulations containing the compound disclosed herein, can be lyophilized to produce a lyophilizate which can be reconstituted with a pharmaceutically acceptable carrier, such as water, to regenerate a liposomal suspension.

Nanoparticle carrier moieties are solid or hollow carriers generally less than a micron in diameter or length. The compound can be encapsulated in, adsorbed onto, or covalently linked to the surface of the nanoparticle carrier moiety. The nanoparticle, which can also be referred to as a scaffold, can comprise a variety of inorganic materials including, but not limited to, metals, semi-conductor materials or ceramics. Preferred metal-based compounds for the manufacture of nanoparticles include titanium, titanium dioxide, tin, tin oxide, silicon, silicon dioxide, iron, iron(III) oxide, silver, gold, copper, nickel, aluminum, steel, cobalt-chrome alloys, cadmium (preferably cadmium selenide) and titanium alloys. Suitable ceramic materials include brushite, tricalcium phosphate, alumina, silica, and zirconia. The nanoparticle can be made from organic materials including carbon (diamond). Suitable polymers include polystyrene, silicone rubber, polycarbonate, polyurethanes, polypropylenes, polymethylmethacrylate, polyvinyl chloride, polyesters, polyethers, and polyethylene. Biodegradable biopolymers (e.g., polypeptides such as BSA, polysaccharides, etc.), other biological materials (e.g., carbohydrates such as hyaluronic acid and chitosan) are also suitable for use as a nanoparticle scaffold. Polymeric compounds can be homopolymers or copolymers prepared from monomers of polymers disclosed herein, wherein the copolymer can be of diblock, triblock, or multiblock structure. Suitable polymers include polyalkylcyanoacrylate (PACA) (Bertling et al., *Biotechnol. Appl. Biochem.* 13:390 (1991)); polybutylcyanoacrylate (PBCA) (Chavany et al., *Pharm. Res.* 9:441 (1992)); polybutylcyanoacrylate with the peptide-drug complex absorbed onto the surface and coated with polysorbate 80 (Kreuter et al., *Brain Res.* 674:171 (1995), Kreuter, *Adv. Drug Deliv. Rev.* 47:65 (2001), Kreuter, *Curr. Med. Chem.* 2:241 (2002)); polyisohexylcyanoacrylate (PIHCA) (Chavany et al., *Pharm. Res.* 11:1370 (1994)); polyhexylcyanoacrylate (PHCA) (Zobel et al., *Antisense Nucleic Acid Drug Dev.* 7:483 (1997)); and PEGylated polycyanoacrylate (Pilar et al., *Pharm. Res.* 18:1157 (2001)), poly(lactide-co-glycolides), poly(lactic acid), poly(alkylene glycol), poly(methylmethacrylate-co-methacrylic acid), polyallylamine, polyanhydride, polyhydroxybutyric acid, or polyorthoesters and the like. Other nanoparticle materials are described in U.S. Pat. Nos. 7,371,738; 7,332,586; 7,332,159; 7,304,045; 7,285,289; 7,259,252; 6,797,380; 6,689,338; 6,602,932; 6,521,431; and 6,475,995, each herein incorporated by reference in its entirety.

Nanoparticles are available commercially or can be conveniently produced by known methods, including emulsion polymerization in a continuous aqueous phase, emulsion polymerization in continuous organic phase, interfacial polymerization, solvent deposition, solvent evaporation, dissolution of an organic polymer solution, cross-linking of water-soluble polymers in emulsion, dissolution of macromolecules, carbohydrate cross-linking, progressive nucleation in solution (e.g., by colloid reaction), or by various physical and chemical vapor deposition processes, such as sputter deposition. See, e.g., Hayashi, *Vac. Sci. Technol.* A5:1375 (1987); Hayashi, *Physics Today* December, pp. 44 (1987); MRS Bulletin, January 1990, pgs. 16-47.

Alternatively, nanoparticles can be produced using $HAuCl_4$ and a citrate-reducing agent, using methods known in the art. See, e.g., Marinakos et al., *Adv. Mater.* 11:34 (1999); Marinakos et al., *Chem. Mater.* 10:1214 (1998); Enustun et al., *J. Am. Chem. Soc.* 85:3317 (1963). Tin oxide nanoparticles having a dispersed (in $H_2O$) aggregate particle size of about 140 nm are available commercially from Vacuum Metallurgical Co., Ltd. of Chiba, Japan. Other commercially available nanoparticles of various compositions and size ranges are available, for example, from Vector Laboratories, Inc. of Burlingame, Calif.

Besides sputter deposition, plasma-assisted chemical vapor deposition (PACVD) is another technique that can be used to prepare suitable nanoparticles. PACVD functions in relatively high atmospheric pressures (on the order of one torr and greater) and is useful for generating particles having diameters of about 1000 nanometers and smaller. For example, aluminum nitride particles having diameters of less than 1000 nanometer can be synthesized by PACVD using Al(CH$_3$)$_3$ and NH$_3$ as reactants. The PACVD system typically includes a horizontally mounted quartz tube with associated pumping and gas feed systems. A susceptor is located at the center of the quartz tube and heated using a 60 KHz radio frequency source. The synthesized aluminum nitride particles are collected on the walls of the quartz tube. Nitrogen gas is commonly used as the carrier of the Al(CH$_3$)$_3$. The ratio of Al(CH$_3$)$_3$:NH$_3$ in the reaction chamber is controlled by varying the flow rates of the N$_2$/Al(CH$_3$)$_3$ and NH$_3$ gas into the chamber. A constant pressure in the reaction chamber of 10 torr is generally maintained to provide deposition and formation of the ultrafine aluminum nitride nanoparticles. PACVD can be used to prepare a variety of other suitable nanoparticles.

A nanoparticle can further contain a polymer that affects the charge or lipophilicity or hydrophilicity of the particle. Any biocompatible hydrophilic polymer can be used for this purpose, including but not limited to, poly(vinyl alcohol).

The present invention is explained in greater detail in the following non-limiting Examples.

Example 1

Study of Neuropathic Pain in Patients with Cancer

A Phase 2, multicenter, placebo-controlled, randomized, parallel group study was carried out to evaluate the safety, efficacy, and dose-response of KRN5500 in patients with end-stage cancer experiencing neuropathic pain. Nineteen (19) patients were enrolled in the study. Thirteen were randomized to receive KRN5500 and 6 were randomized to receive placebo. Due to a randomization error at an investigative site, one patient randomized to receive KRN5500 actually received placebo. Of the 12 patients who received KRN5500, 3 (25%) completed all dosing visits. Two (28.6%) of the patients who received placebo completed all dosing visits. No patients were lost to follow up and no patients died.

The treatment groups were similar in demographics, with the majority of patients being Caucasian (73.7%) and approximately 50/50 in distribution by gender. The median age of patients enrolled was 62 years, ranging from 41 to 84 years. The average body surface area (BSA) was 1.8 m$^2$ ranging from 0.95 to 2.27 m$^2$. The majority of the patient population had allodynia (84.2%). This and other baseline characteristics of neuropathic pain were consistent between the treatment groups.

The median duration of exposure to KRN5500 was 40 days compared to 29 days for placebo. On average, KRN5500 patients took 5.3 doses while placebo patients took 4.4 doses. The highest dose received was 2.2 mg/m$^2$. Seven (58.3%) of KRN5500 patients were exposed to at least one dose at this level, while 4 (57.1%) of Placebo patients were exposed to at least one dose at this level.

Efficacy Results

Pain intensity, based on clinic numeric rating scale (NRS) scores, was analyzed for both the Intent-to-treat (ITT) and modified efficacy (ME) populations. Results were similar in both analyses with the KRN5500 group exhibiting a median decrease from baseline of 22% (ITT) and 23.6% (ME) while the median change in the Placebo group was zero (0) for both analyses. Based on a Wilcoxon Rank Sum test of the medians, the decrease in pain intensity was statistically significant in the ME analysis (p=0.03). Since more than 80% of patients had allodynia as a baseline characteristic, results from the analysis of the subset of patients with allodynia present at baseline was consistent with the overall analysis. Too few patients presented without allodynia at baseline to adequately draw conclusions in this subset. Analysis of best pain intensity response (largest decrease in pain) recorded in clinic over all doses indicate that patients treated with KRN5500 had a median decrease of 29.3% while patients treated with placebo showed no decrease. Decreases in pain intensities based on the diary data were similar to those observed in the clinic, with the KRN5500 treatment group showing a median decrease of 16.4% while the Placebo treatment group showed no decrease. Overall, 5 (42%) of KRN5500 treated patients showed a 20% or greater reduction in pain intensity, based on diary endpoint, while only 1 (14%) of the patients treated with Placebo achieved this level. Three (25%) of the KRN5500 treated patients achieved 33% or greater pain decrease and none of the placebo patients achieved this level. When evaluated for the last dose received (Endpoint), there was no trend for dose response of KRN5500 in either the ITT or ME population analysis.

The neuropathic pain questionnaire (NPQ) scores were obtained at each clinic visit; however, an error discovered in the wording of anchors for questions 9 and 10 invalidated the use of the discriminant function score for predicting neuropathic pain; individual questions from the NPQ were as well as evaluating efficacy of treatment. As a result, the function scores and questions 9 and 10 were not summarized. Burning pain, electric pain and freezing pain showed decreases from baseline in favor of KRN5500. However other NPQ questions related to sensitivity to touch, shooting pain, numbness, tingling, or squeezing pain were no different between treatment groups. In addition, no treatment differences were observed for increased pain due to touch or to weather changes. With exception of burning pain, changes from baseline of individual NPQ questions varied greatly from week to week, suggesting that the NPQ was not a sensitive measure of efficacy.

Patient perception of pain at its least in the past 24 hours and the aggregate measure of pain's interference in the last 24 hours were the only brief pain inventory (BPI) measures that showed a demonstrable difference between treatment groups. Both measures showed decreases from baseline for the KRN5500 treated patients, whereas there was no change in the Placebo treated patients.

Of the two questions regarding brush/touch induced pain and cold induced pain, only the "brush/touch" portion of the supplemental pain questionnaire (SPQ) was consistent with NRS scores with the KRN5500 treated patients showing a greater decrease in pain scores than the Placebo treated patients. The "cold induced pain" portion of the SPQ showed no treatment differences as both treatment group show decreases in cold induced pain at endpoint.

Treatment differences were observed for both dynamic and cold allodynia assessment. The KRN5500 treated patients showed a larger decrease in pain associated with both touch and cold. Both the affected and unaffected areas showed a response to KRN5500. This was due, in some instances, to site errors in choosing a body area (as the unaffected area for assessment) that had allodynia to a lesser degree than the affected area. This resulted in baseline allodynia scores in the unaffected areas that could show response to study treatment.

At baseline, patients had relatively high median Karnofsky Performance Status (KPS) of 75 (KRN5500 patients) and 80 (placebo patients) indicating that patients were able to function independently with some effort. This measure of performance did not change throughout the study for either treatment group.

At the 1 week post-dose follow up, aggregated physical and mental SF-12 scores were basically unchanged from baseline. In addition, there were no treatment differences observed for either component.

Safety Results

All patients treated with KRN5500 (100%) had at least one treatment emergent adverse event, compared to 86% (6 of 7 patients) in the Placebo treated group. Events recorded by the KRN5500 patients tended to be more severe (84% moderate or severe in KRN5500 vs. 71% in Placebo). Events were typically gastrointestinal disorders such as nausea or vomiting and were more frequently considered to be related to treatment in the KRN5500 group than in the Placebo group (92% vs. 14%). Three patients (25%) in the KRN5500 group and 1 (14%) patient in the Placebo group experienced serious adverse events (AEs). None were considered to be related to study drug. Two patients treated with KRN5500 withdrew from the study due to nausea and vomiting which were thought to be related to study drug. One patient treated with KRN5500 withdrew due to convulsions not thought to be related to study drug. One patient treated with Placebo withdrew from the study due to a stroke not related to study drug. No deaths were observed.

As a whole, clinically significant laboratory abnormalities, changes in vital signs, changes in physical examinations, or changes in ECGs were not observed throughout the study.

No patients were tapered from opiates in this study; therefore no assessment of clinical opiate withdrawal was made.

CONCLUSIONS

KRN5500 demonstrated a statistically significant decrease in pain intensity as measured by NRS in the clinic. Results from patient diaries were consistent with clinic evaluations. The NPQ was not sensitive as a measure of efficacy. In addition, the "cold induced pain" portion of the SPQ showed no treatment effect, while the BPI and "brush/touch" portion of the SPQ were consistent with the Clinic NRS measures.

High incidences of nausea and vomiting were observed in the KRN5500 treatment group and were generally considered to be related to study drug. These events were the reason for withdrawal of 2 patients. Of the serious AEs recorded, none were thought to be related to study drug. Laboratory, vital signs, ECG and physical exam assessment showed no clinically significant changes throughout the study.

Example 2

Formulation of KRN5500

A nanoemulsion formulation for intravenous administration was developed for KRN5500. The components of the formulation are listed in Table 1 by weight %. This formulation is expected to produce fewer side effects in the form of gastrointestinal disturbances as compared to KRN5500 formulations used previously.

TABLE 1

| Component | Amount |
|---|---|
| KRN5500 | 0.2 |
| Soybean oil | 7.0 |
| MIGLYOL 812 | 7.0 |
| Soy lecithin (PL90G) | 7.0 |
| Sodium oleate | 0.3 |
| EDTA disodium dehydrate | 0.006 |
| Sucrose, NF grade | 17.0 |
| pH (adjusted with HCl/arginine) | 6.2 ± 0.1 |
| Water For Injection, USP | QS |
| Total | 100 |

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

What is claimed is:

1. A pharmaceutical composition comprising a compound of Formula II:

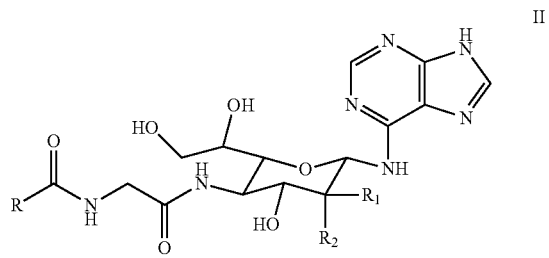

wherein $R_1$ represents H and $R_2$ represents OH, and R represents an unsubstituted alkyl or alkenyl;
or a pharmaceutically acceptable salt or optical isomer thereof;
and pharmaceutically acceptable carriers;
wherein the pharmaceutical composition is a nanoemulsion comprising an aqueous phase, an oil phase, and a surfactant, wherein the nanoemulsion comprises about 10, 11, 12, 13, or 14 weight % oil phase.

2. The pharmaceutical composition of claim 1, comprising about 7 weight % soybean oil, about 7 weight % capric/caprylic acid triglyceride, about 7 weight % soy lecithin, about 0.3 weight % sodium oleate, about 0.006 weight % EDTA, about 17 weight % sucrose, and about 62 weight % water.

3. The pharmaceutical composition of claim 1, further comprising a buffer and having a pH of about 5 to about 7.

4. The pharmaceutical composition of claim 1, further comprising a chelator and a tonicity modifier.

5. The pharmaceutical composition of claim 1, wherein R is an unsubstituted alkenyl having 1-24 carbon atoms.

6. The pharmaceutical composition of claim 5, wherein said unsubstituted alkenyl is a linear alkenyl having 11-13 carbon atoms.

7. The pharmaceutical composition of claim 5, wherein R is an unsubstituted alkenyl having the structure:

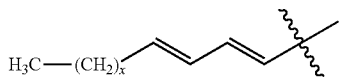

wherein x denotes an integer from 1-19.

8. The pharmaceutical composition of claim 7, wherein x denotes an integer from 6-8.

9. The pharmaceutical composition of claim 8, wherein the compound is 6-[4-deoxy-4-[(2E,4E)-tetradecadienoylglycyl]amino-L-glycero-p-L-manno heptopyranosyl]amino-9H-purine (KRN5500).

10. A method for treating neuropathic pain in a subject, comprising administering to a subject in need thereof, the pharmaceutical composition of claim 1.

11. The method of claim 10, wherein said neuropathic pain is due to a neuropathy selected from the group consisting of chemotherapy-induced neuropathy, cancer-related neuropathy, HIV-related peripheral neuropathy, post-herpetic neuralgia, diabetic neuropathy, sciatica, fibromyalgia, chronic fatigue syndrome pain, multiple sclerosis pain, complex regional pain syndrome type I, complex regional pain syndrome type II, central pain syndrome, painful traumatic mononeuropathy, post surgical pain syndrome, post mastectomy syndrome, post thoracotomy syndrome, phantom pain, nerve root avulsion, post radiation neuropathy, repetitive movement nerve injury, repetitive stress injury, and post injury neuropathy.

* * * * *

UNITED STATES PATENT AND TRADEMARK OFFICE
CERTIFICATE OF CORRECTION

PATENT NO. : 9,248,098 B2
APPLICATION NO. : 13/122771
DATED : February 2, 2016
INVENTOR(S) : Didsbury et al.

It is certified that error appears in the above-identified patent and that said Letters Patent is hereby corrected as shown below:

In the Claims:

Column 30, Line 49, "10, 11, 12, 13, or 14 weight % oil phase" should read --7 weight % soybean oil, about 7 weight % capric/caprylic acid triglyceride, about 7 weight % soy lecithin, about 0.3 weight % sodium oleate, and about 62 weight % water--

Column 31, Line 12, "glycero-[p]-L-manno" should read --glycero-β-L-manno--

Signed and Sealed this
Twelfth Day of July, 2016

Michelle K. Lee
*Director of the United States Patent and Trademark Office*